United States Patent
Gumiero

(10) Patent No.: US 9,839,397 B2
(45) Date of Patent: Dec. 12, 2017

(54) MOTION COMPENSATION IN PHOTOPLETYSMOGRAPHY-BASED HEART RATE MONITORING

(71) Applicant: STMICROELECTRONICS S.R.L., Agrate Brianza (IT)

(72) Inventor: Alessandro Gumiero, Chieri (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 14/968,249

(22) Filed: Dec. 14, 2015

(65) Prior Publication Data

US 2017/0164905 A1  Jun. 15, 2017

(51) Int. Cl.
*A61B 5/00* (2006.01)
*A61B 5/024* (2006.01)

(52) U.S. Cl.
CPC ........ *A61B 5/7282* (2013.01); *A61B 5/02427* (2013.01); *A61B 5/7225* (2013.01); *A61B 5/7246* (2013.01); *A61B 5/742* (2013.01)

(58) Field of Classification Search
None
See application file for complete search history.

(56) References Cited

U.S. PATENT DOCUMENTS 6,997,879 B1 * 2/2006 Turcott ................ A61B 5/0261
600/336
2014/0213863 A1    7/2014 Loseu et al.

* cited by examiner

Primary Examiner — Brian T Gedeon
(74) Attorney, Agent, or Firm — Seed IP Law Group LLP

(57) ABSTRACT

A method and apparatus for determining a heart rate of a biological body are disclosed. In the method and apparatus, light having a first wavelength and light having a second wavelength are emitted at the biological body. The first wavelength is associated with a first absorption coefficient for blood components and the second wavelength is associated with a second absorption coefficient for the blood components that is less than the first absorption coefficient. A first reflected signal is captured as a result of the light having the first wavelength being reflected from the biological body and a second reflected signal is captured as a result of the light having the second wavelength being reflected from the biological body. A heart rate signal is obtained based on the first and second reflected signals. A heart rate of the biological body is determined based on the heart rate signal.

30 Claims, 9 Drawing Sheets

MOTION COMPENSATION IN PHOTOPLETYSMOGRAPHY-BASED HEART RATE MONITORING

BACKGROUND

Technical Field

The present disclosure relates to photopletysmography (PPG)-based heart rate determination under motion conditions. In particular, the present disclosure relates to a device that compensates motion artifacts introduced in a PPG signal.

Description of the Related Art

PPG-based heart rate monitoring and determination is sensitive to noise artifacts. The noise artifacts can be introduced as a result of movement of a biological body or a heart rate measurement device used to perform the heart rate measurement. The noise corrupts a heart rate signal detected by the heart rate measurement device using PPG techniques. Further, the noise makes heart rate determination unreliable.

BRIEF SUMMARY

A device may be summarized as including: a first light source configured to emit light having a first wavelength at a biological body, the first wavelength being associated with a first absorption coefficient for blood components; a second light source configured to emit light having a second wavelength at the biological body, the second wavelength being associated with a second absorption coefficient for the blood components that is less than the first absorption coefficient; a photodetector configured to capture a first reflected signal as a result of the light having the first wavelength being reflected from the biological body and capture a second reflected signal as a result of the light having the second wavelength being reflected from the biological body; and a processor coupled to the photodetector and configured to receive the first reflected signal and the second reflected signal from the photodetector, obtain a heart rate signal as a difference between the first reflected signal and the second reflected signal and determine a heart rate of the biological body based on the heart rate signal.

The processor may be further configured to: obtain an amplitude adapting coefficient for the second reflected signal; and obtain the heart rate signal as a difference between the first reflected signal and a quotient of the second reflected signal and the amplitude adapting coefficient. The amplitude adapting coefficient may be a divisor of the second reflected signal that minimizes a difference in energy between the first reflected signal and the quotient of the second reflected signal and the amplitude adapting coefficient. The processor may be further configured to: cross-correlate the first reflected signal and the second reflected signal to produce a cross-correlation function between the first reflected signal and the second reflected signal; identify a maximum of the cross-correlation function; identify a time index corresponding to the maximum of the cross-correlation function; and shift the second reflected signal by the time index prior to obtaining the heart rate signal using the second reflected signal shifted by the time index. The processor may be further configured to: low-pass filter the first reflected signal and the second reflected signal; and de-trend the first reflected signal and the second reflected signal. A cutoff frequency of the low pass filter may be 4 Hertz or lower. The device may further include a motion detector coupled to the processor and configured to output a signal to the processor indicating whether the device was displaced, wherein: the processor is further configured to determine the heart rate based on the heart rate signal if the signal to the processor indicates that the device was displaced. The device may further include an output device coupled to the processor and configured to receive the heart rate from the processor and display the heart rate.

A method may be summarized as including: emitting light having a first wavelength at a biological body, the first wavelength being associated with a first absorption coefficient for blood components; capturing a first reflected signal as a result of the light having the first wavelength being reflected from the biological body; emitting light having a second wavelength at the biological body, the second wavelength being associated with a second absorption coefficient for the blood components that is less than the first absorption coefficient; capturing a second reflected signal as a result of the light having the second wavelength being reflected from the biological body; obtaining a heart rate signal as a difference between the first reflected signal and the second reflected signal; and determining a heart rate of the biological body based on the heart rate signal.

The method may further include: scaling the second reflected signal by a reciprocal of an amplitude adapting coefficient before obtaining the heart rate signal as the difference between the first reflected signal and the second reflected signal using the second reflected signal scaled by the reciprocal of the amplitude adapting coefficient. The amplitude adapting coefficient may be a divisor of the second reflected signal that minimizes a difference in energy between the first reflected signal and the quotient of the second reflected signal and the amplitude adapting coefficient. The method may further include: time shifting the second reflected signal prior to obtaining the heart rate signal using the time shifted second reflected signal. The second reflected signal may be shifted by a time index corresponding to a maximum cross-correlation value between the first reflected signal and the second reflected signal. The method may further include: filtering the first and second reflected signals; and de-trending the first and second reflected signals.

A system may be summarized as including: a first light source; a second light source; a photodetector; a processor; and a computer-readable storage medium having stored thereon instructions that, when executed by the processor, cause the processor to: instruct the first light source to emit light having a first wavelength at a biological body, the first wavelength being associated with a first absorption coefficient for blood components; instruct the second light source to emit light having a second wavelength at the biological body, the second wavelength being associated with a second absorption coefficient for the blood components that is less than the first absorption coefficient; receive a first reflected signal captured by the photodetector as a result of the light having the first wavelength being reflected from the biological body and a second reflected signal captured by the photodetector as a result of the light having the second wavelength being reflected from the biological body; obtain a heart rate signal based on the first reflected signal and the second reflected signal; and determine a heart rate of the biological body based on the heart rate signal.

The instructions may further cause the processor to obtain the heart rate signal as a difference between the first reflected signal and the second reflected signal. The instructions may further cause the processor to: obtain an amplitude adapting coefficient for the second reflected signal; adjust an amplitude of the second reflected signal by the amplitude adapting coefficient to obtain an amplitude-adjusted second reflected signal; and obtain the heart rate signal as a difference between the first reflected signal and the amplitude-adjusted second reflected signal. The instructions may further cause the processor to: low-pass filter the first and second reflected signals to respectively produce first and second filtered signals; and de-trend the first and second filtered signals ahead of obtaining the heart rate signal. The first wavelength may be between 500 and 580 nanometers (nm) and the second wavelength may be between 680 and 700 nm.

DETAILED DESCRIPTION

Figure 1:
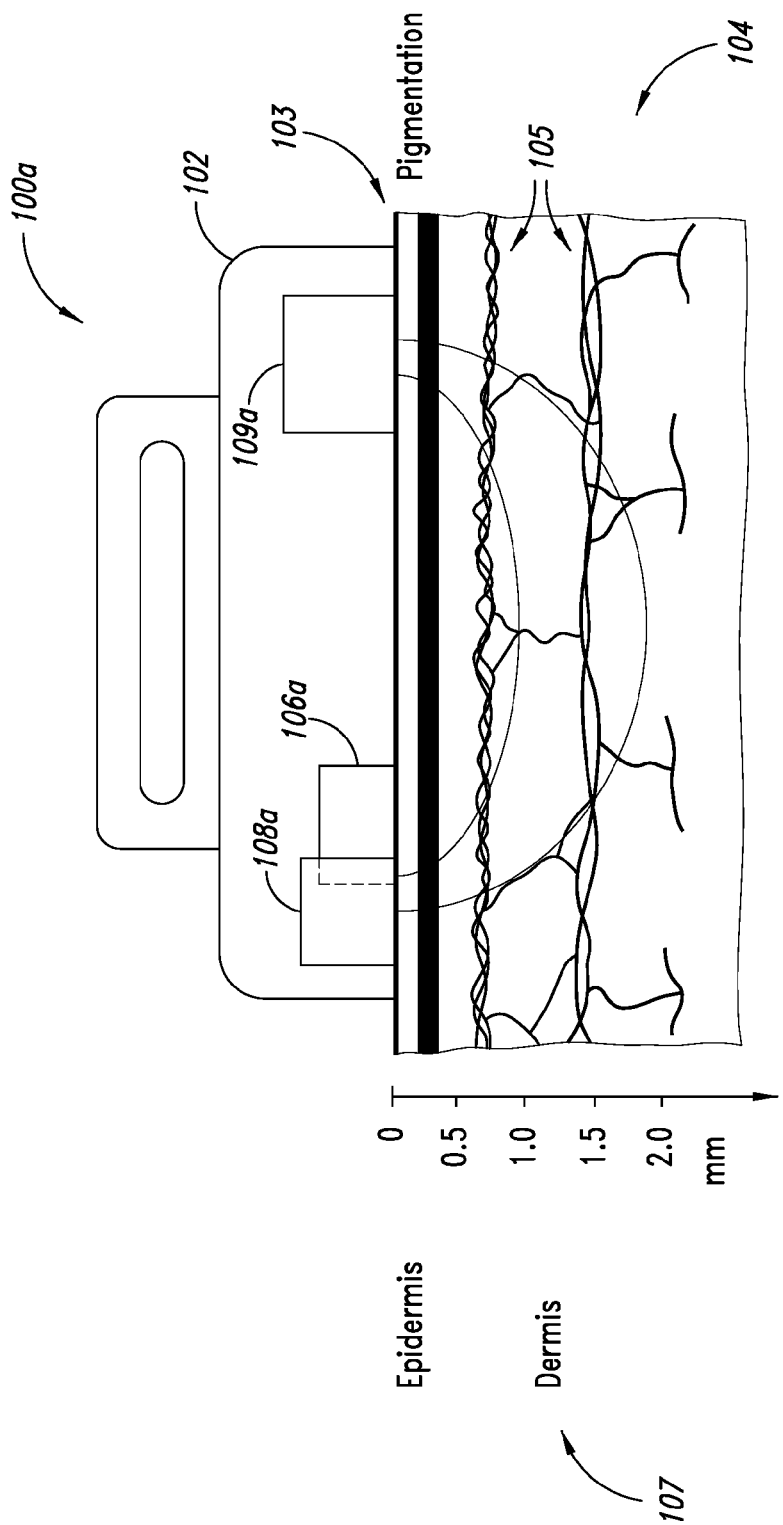
FIG. 1 shows a cross-sectional view of a probe of a heart rate measurement device positioned near the skin of a biological body.

FIG. 1 shows a cross-sectional view of heart rate measurement device $100a$ positioned near the skin $103$ of a biological body $104$. The heart rate measurement device $100a$ is used to measure the heart rate of the biological body $104$ using photopletysmography (PPG). The heart rate measurement device $100a$ includes a probe $102$ having a first light source $106a$, a second light source $108a$ and a photodetector $109a$. The probe $102$ is positioned near the skin $103$ of the biological body $104$ (and may, for example, be in contact with the skin $103$). Light emanating from the first light source $106a$ and the second light source $108a$ is captured by the photodetector $109a$ after having at least partially penetrated the biological body $104$ and been reflected by the biological body $104$.

PPG is a non-invasive technique for heart rate measurement and detection. PPG relies on the principle that blood components, such as oxyhemoglobin and deoxyhemoglobin, reflect back light having certain wavelengths. Light emitted by the first light source $106a$ or the second light source $108a$ will reach a blood vessel $105$ in the dermis $107$. Blood components reflect light having certain wavelengths (for example, green light of 500-550 nanometers (nm) and yellow light of about 580 nm) differently than light having other wavelengths (for example, red light of a wavelength slightly lower than 700 nm). The intensity of light reflected from the biological body changes due to the different absorption coefficients of the colors of light. The intensity of reflected light depends on the volume of blood in a vessel. When the volume of blood in vessel is relatively large the reflected light intensity is low (because the blood absorbs more light) and vice-versa. This variation is correlated with blood flow. Green light is a lot more sensitive to blood than red light because of its associated higher absorption coefficient. The variation of the received light intensity over time is due to volumetric variations.

PPG-based heart rate measurements are sensitive to movement of the biological body $104$ or the heart rate measurement device $100a$ during measurement. For example, movement of the biological body $104$ while a heart rate measurement is being made changes the area of the dermis $107$ on which light is shone. As a result of the movement, noise is introduced in the reflected signal. Similarly, movement of the probe $102$ (or light source emanating light having a wavelength or photodetector $109a$ thereof) also introduces noise in the reflected signal.

The heart rate measurement device $100a$ compensates for the noise, or in general artifacts, introduced in the reflected signal as a result of the movement. The heart rate measurement device $100a$ compensates for the noise by utilizing two light sources that emit light having different wavelengths, whereby one light source (referred to herein as the "first light source") has a wavelength with relatively high absorption coefficient for blood components and another light source (referred to herein as the "second light source") has a wavelength with relatively low absorption coefficient for blood components.

Figure 2:
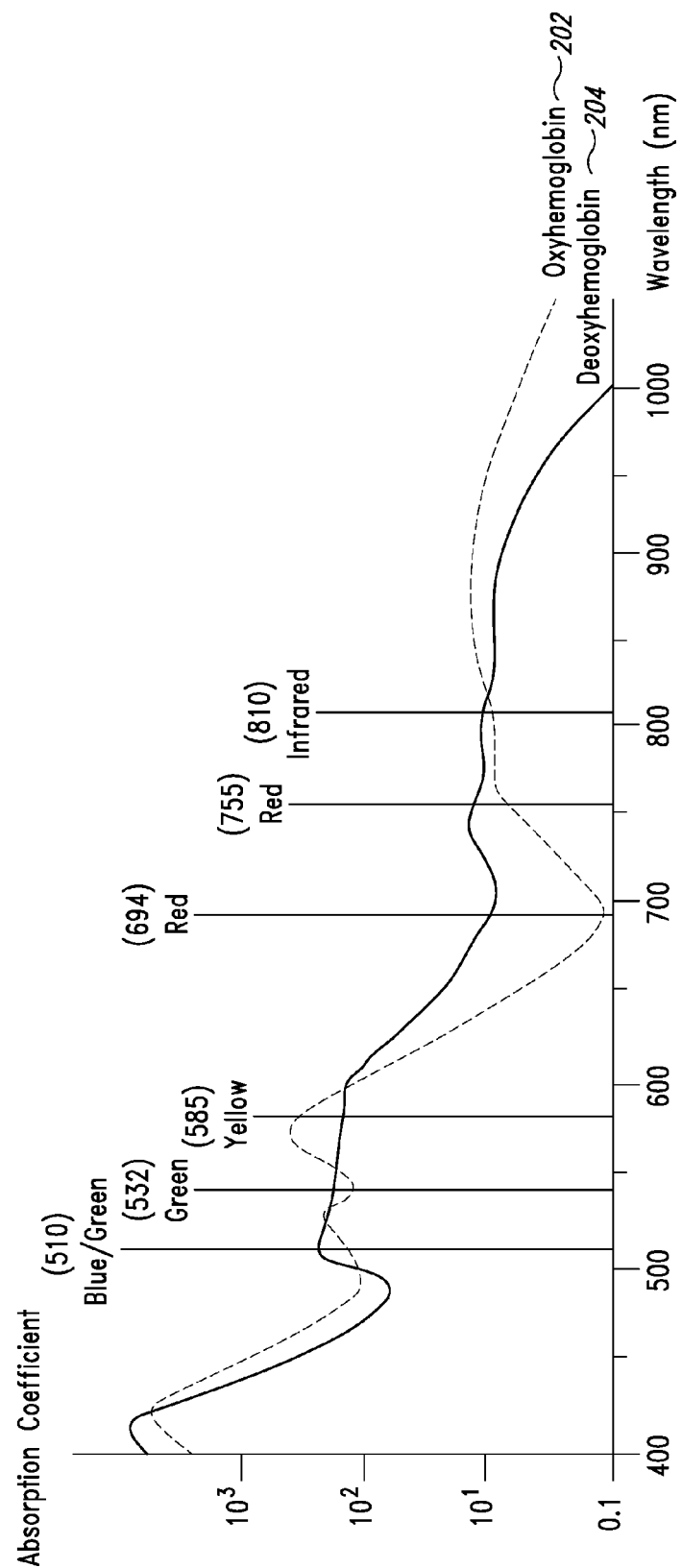
FIG. 2 shows a diagram of the absorption coefficients of blood components for light of different wavelengths.

FIG. 2 shows a diagram of the absorption coefficients of blood components for light of different wavelengths. Graph $202$ shows the absorption coefficients for oxyhemoglobin and graph $204$ shows the absorption coefficients for deoxyhemoglobin for various light wavelengths. The lower is the absorption coefficient, the greater the transparency of the blood component to light. For example, oxyhemoglobin has high transparency for red light (having a wavelength of about 700 nm) as evidenced by the low absorption coefficient of 0.1. Accordingly, more red light is reflected than blue, green or yellow light (wavelengths in the range of 500-600 nm). Blue, green are largely absorbed by oxyhemoglobin and are not reflected.

When the first light source is used to provide light having a wavelength with a high absorption coefficient, the first reflected signal (denoted as $R_1$) has a signal component ($S_1$) that is representative of the heart rate. However, when the second light source is used to provide light having a wavelength with a low absorption coefficient, the second reflected signal (denoted as $R_2$) has a weak signal component ($S_2$) that is not representative of the heart rate because the light is not reflected by the blood components. However, the noise components ($N_1$ and $N_2$) of the respective first and second reflected signals are similarly affected by movement.

By modeling the first reflected signal as $R_1=S_1+N_1$ and the second reflected signal as $R_2=S_2+N_2$, the difference between the reflected signals is represented as:

$$R_2=S_1+N_1-(S_2+N_2)=(S_1-S_2)+(N_1-N_2) \qquad \text{Equation (1).}$$

Because the signal component of the second reflected signal ($S_2$) is not reflected by the blood components, $S_2$ may not influence the signal term ($S_1-S_2$) of equation (1). The signal term may be simplified as: $S_1-S_2 \approx S_1$. The noise components are both similarly affected by movement of the biological body or the heart rate measurement device $100a$. The noise components should substantially cancel one another out. That is, $N_1-N_2 \approx 0$. Accordingly, obtaining the difference between the first reflected signal and the second reflected signal may improve the received signal component used to determine the heart rate of the biological body. That is:

$$R_1-R_2 \approx S_1 \qquad \text{Equation (2).}$$

Figure 3:
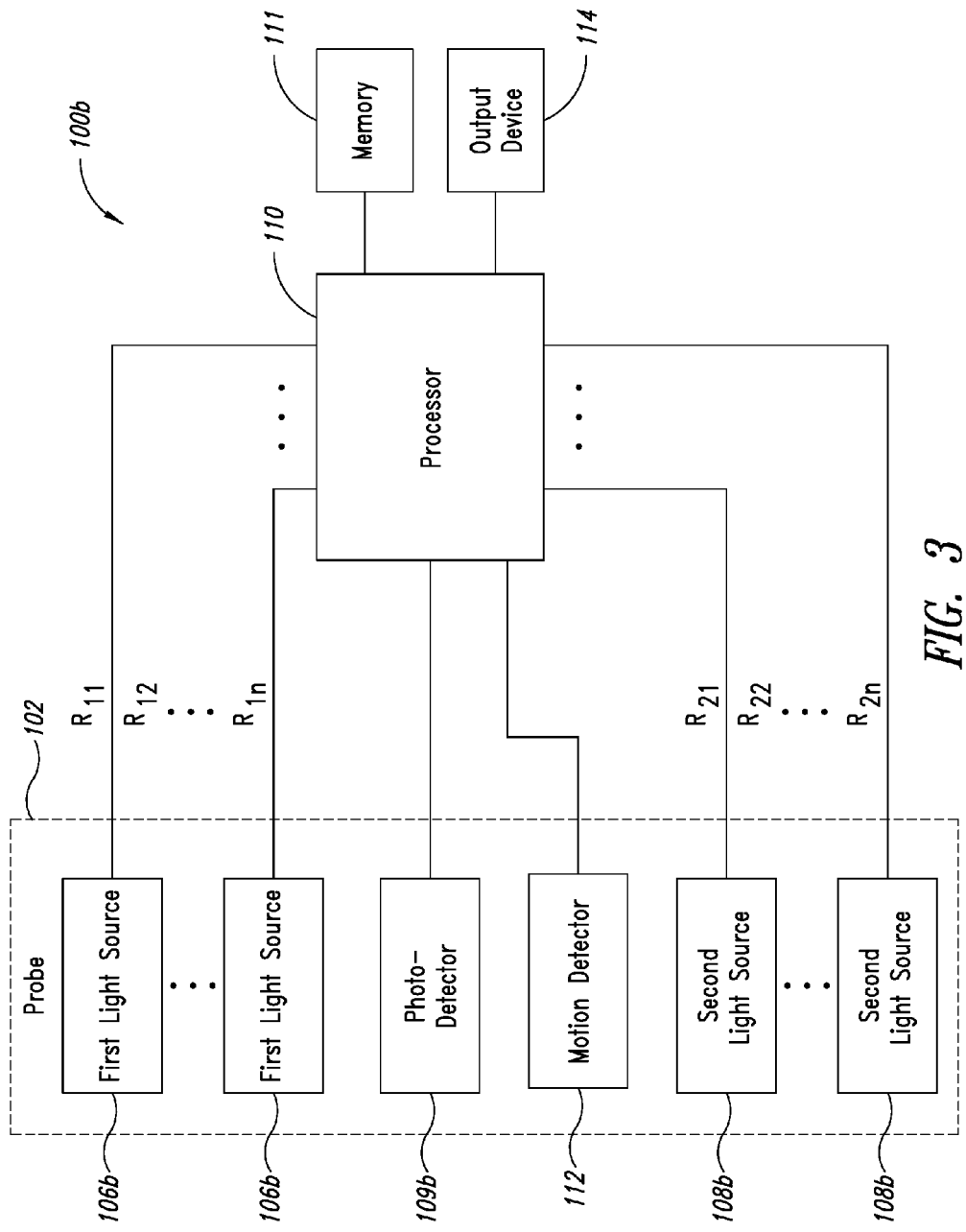
FIG. 3 shows a block diagram of a heart rate measurement device.

FIG. 3 shows a block diagram of a heart rate measurement device 100b. The heart rate measurement device 100b comprises a processor 110, memory 111, one or more first light sources 106b, one or more second light sources 108b, a photodetector 109b, a motion detector 112 and an output device 114. The one or more first light sources 106b and the one or more second light sources 108b may each be a light emitting diode (LED). Further, the photodetector 109b may be a photodiode and the motion detector 112 may be an accelerometer or a gyroscope. In addition, the processor 110 may be any type of device that is capable of performing computing functions. For example, the processor 110 may be a microcontroller, microprocessor or digital signal processor (DSP), among others.

The memory 111 may be any type of memory, such as volatile memory that includes random access memory (RAM), among others or non-volatile memory that includes read only memory (ROM), among others. The memory 111 may be a non-transitory computer-readable memory. The memory 111 may be used to store instructions that, when executed by the processor 110, cause the processor 110 to perform the techniques described herein. For example, the memory 111 may store instruction that, when executed by the processor 110, cause the processor 110 to obtain a heart rate signal or determine a heart rate of a biological body as described herein, among others. The output device 114 may be a display, such as a liquid crystal display, or speakers. In various embodiments, the output device 114 may be a communications port for transferring heart rate measurements to another device.

Although not shown in FIG. 3, the heart rate measurement device 100a may include a front end (for example, an analog front end) disposed between the processor 110 and the photodetector 109b. The front end may condition or amplify a signal received from the photodetector 109b and correct acquisition of the signal received from the photodetector 109b. In some embodiments, the front end may be part of the processor 110, whereby the processor amplifies, conditions or corrects the acquisition of the signal from the photodetector 109b.

The heart rate measurement device 100a is used to measure the heart rate of a biological body using PPG as described herein. The one or more first light sources 106b, one or more second light sources 108b, photodetector 109b and motion detector 112 may be part of the probe 102 of the heart rate measurement device 100b.

The one or more first light sources 106b, one or more second light sources 108b, photodetector 109b, motion detector 112 and output device 114 are coupled to the processor 110. The processor 110 sends a first control signal to the one or more first light sources 106b instructing the one or more first light sources 106b to emit light having a first wavelength. As described herein, the emitted light may be blue, green or yellow light that has a relatively high absorption coefficient for blood. The first control signal may indicate the period of time for which the light should be emitted or a first light source 106b may be configured to emit the light for the period of time in response to receipt of the first control signal.

The photodetector 109b then captures the first reflected signal resulting from reflection of the first wavelength light by the biological body. The photodetector 109b outputs the captured first reflected signal to the processor 110.

The processor 110 then sends a second control signal to the one or more second light sources 106 instructing the one or more second light sources 106b to emit light having a second wavelength. As described herein, the emitted light may be red and may have a relatively low absorption coefficient by blood components. The second control signal may indicate the period of time for which the light should be emitted or a second light source 108b may be configured to emit the light for the period of time in response to receipt of the second control signal. The photodetector 109b then captures the second reflected signal resulting from reflection of second wavelength light by the biological body. The photodetector 109b transmits the second reflected signal to the processor 110. The second reflected signal may be identified as such due to the fact that it has been captured at the same time as or subsequent to emitting light by the second light source 108b.

In one embodiment, the heart rate measurement device 100b includes only one first light source 106b and only one second light source 108b. In this case, the first light source 106b and the second light source 108b may alternate emitting light one at a time with an interval for a break therebetween. The positions of the first light source 106b and the second light source 108b may be equidistant from the photodetector 109b. For example, each light source 106b, 108b may be 3 millimeters (mm) to 5 mm from the photodetector 109b. The distance between each light source 106b, 108b and the photodetector 109b may be set to 4 mm. The first light source 106b and the second light source 108b may be positioned on opposite sides of the photodetector 109b or on the same side. The distance between the first light source 106b and the photodetector 109b may be the same as the distance between the second light source 108b and the photodetector 109b. Further, the first light source 106b and the second light source 108b may be positioned in close proximity to one another (for example, abutting or less than 1 mm apart) and on the same side of the photodetector 109b.

In another embodiment, the heart rate measurement device 100b includes two or more first light sources 106b and two or more second light sources 108b, whereby only one of the first light sources 106b and second light sources 108b emits light at a time. When two or more first light sources 106b and two or more second light sources 108b are used, the second and subsequent light sources of the two or more second light sources 108b may be positioned on opposite sides of the photodetector 109b as compared to the first of the two or more second light sources 108b. However, it may be necessary to have at least one pair (comprising a first light source 106b and a second light source 108b) positioned adjacent to each other or within close proximity of each other.

The motion detector 112 detects whether the heart rate measurement device 100b or light sources 106b, 108b or photodetector 109b thereof were moved during the capturing of the reflected signals. If movement is detected, the motion detector 112 sends a signal to the processor 110 indicating that movement was detected. Receipt of the signal by the processor 110 triggers the processor to perform motion compensation using the first and second reflected signals as described herein.

Figure 4:
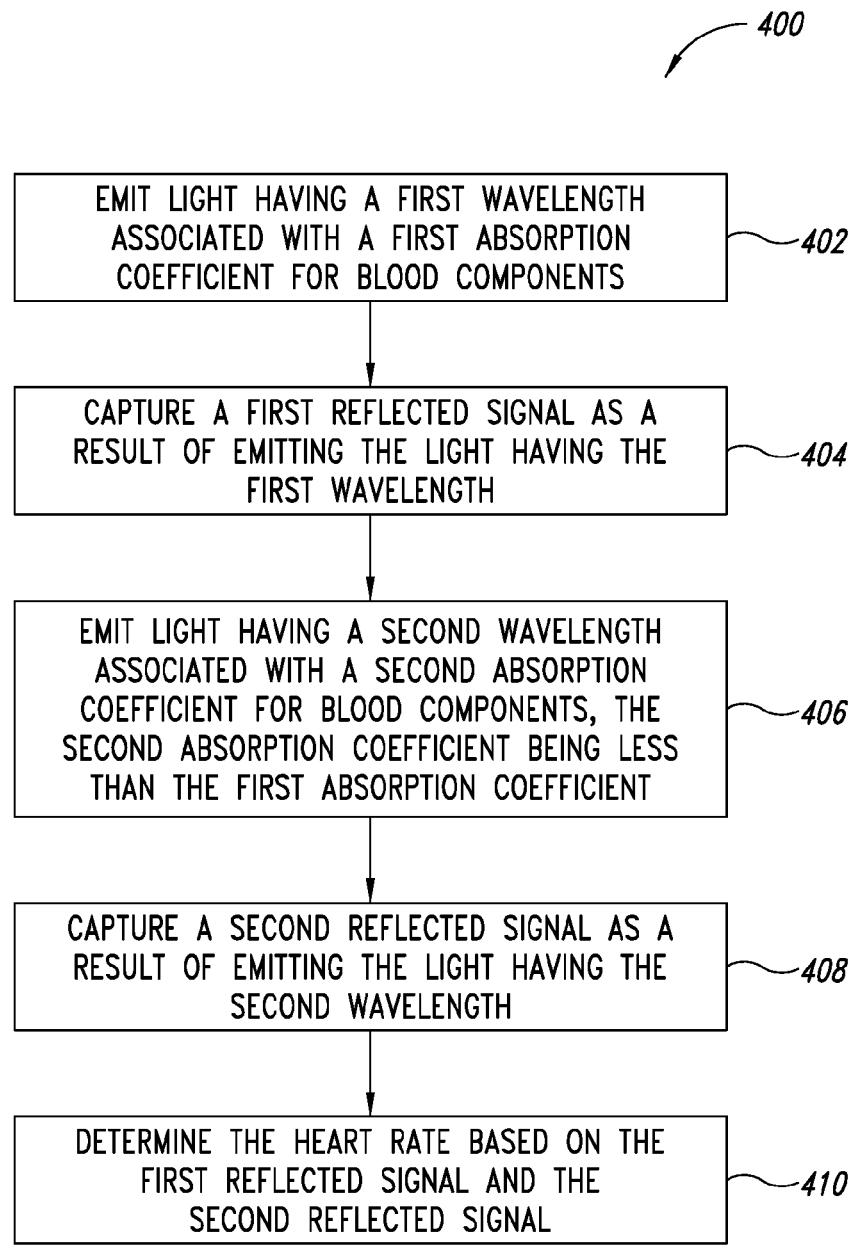
FIG. 4 shows a method for determining the heart rate of a biological body.

FIG. 4 shows a method 400 for determining the heart rate of a biological body. In the method 400, the first light source 106b, at 402, emits light having a first wavelength associated with a first absorption coefficient for blood components. At 404, the photodetector 109b captures the first reflected signal as a result of emitting the light having the first wavelength. Then, at 406, the second light source 108b emits light having a second wavelength associated with a second absorption coefficient for blood components. The second absorption coefficient is less than the first absorption coefficient. At 408, the photodetector 109b captures a second reflected signal as a result of emitting the light having the second wavelength. The first reflected signal and the second reflected signal are provided to the processor 110. In turn, the processor 110, at 410 determines the heart rate based on a difference between the first reflected signal and the second reflected signal. It will of course be understood that the steps in FIG. 4 could be performed in many different orders, such as performing steps 406 and 408 before steps 402 and 404.

Figure 5A:
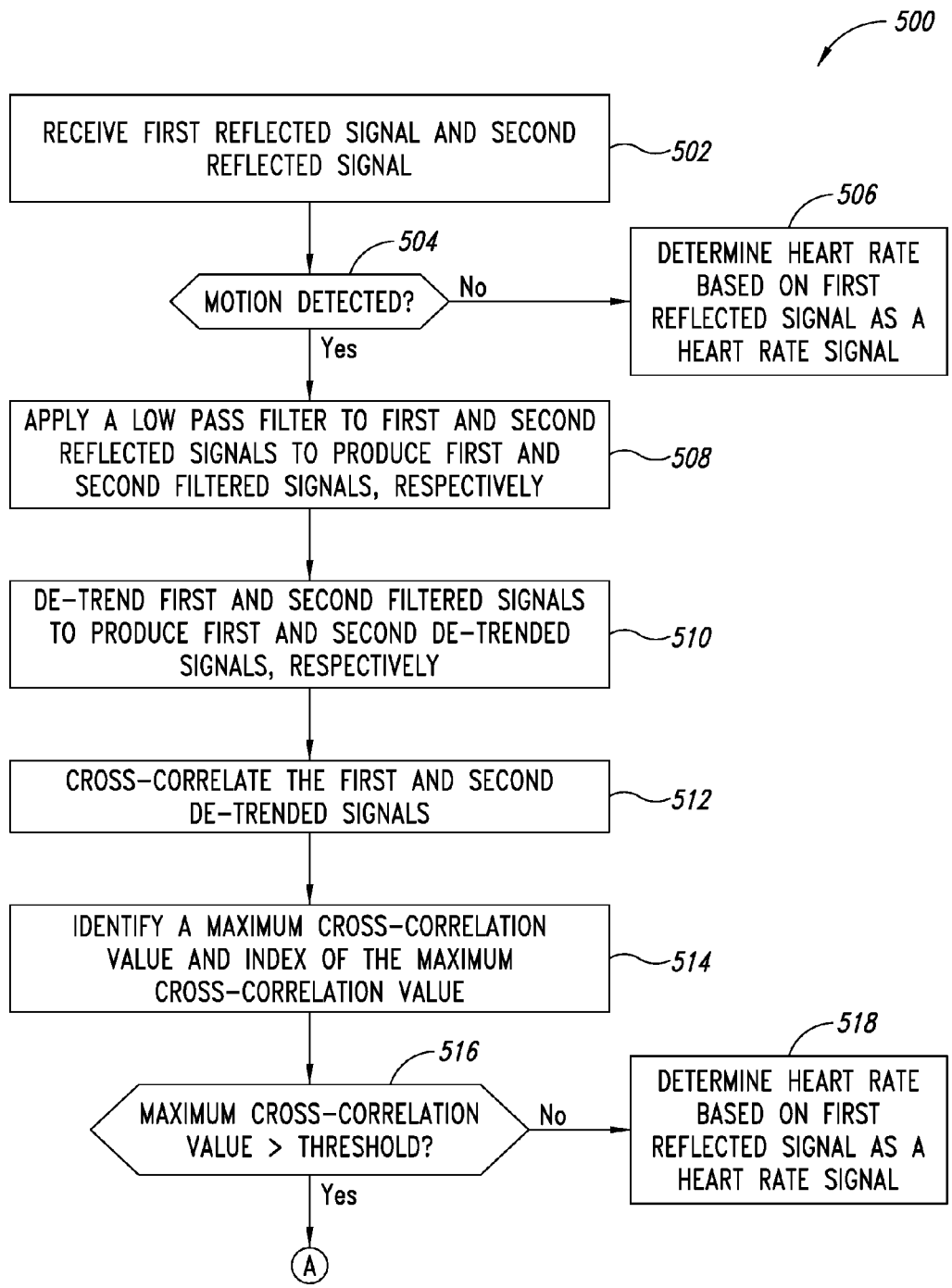
FIGS. 5A and 5B show a flow diagram of a method for compensating for motion in the heart rate measurement device.
Figure 5B:
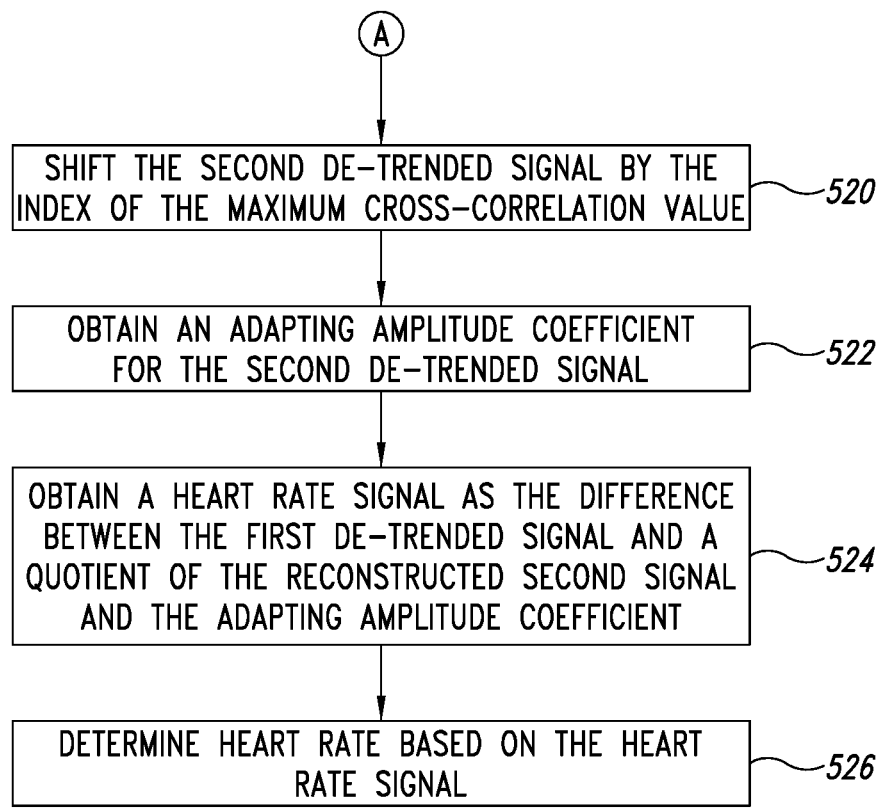

FIGS. 5A and 5B show a flow diagram of a method for compensating for motion in the heart rate measurement device 100b. In the method 500, at 502, the processor 110 receives the first reflected signal and the second reflected signal. The first reflected signal may have been captured by the photodetector 109b as a result of reflection of light emitted by the first light source 106b and the second reflected signal may have been captured by the photodetector 109b as a result of light emitted by the second light source 108b. The processor 110 then determines, at 504, whether motion has been detected. Determining whether motion is detected may be based on the output of the motion detector 112. If motion is not detected, then motion compensation is not necessarily performed. The processor 110, at 506, determines the heart rate based on the first reflected signal as a heart rate signal.

Conversely, if motion is detected, the processor 110 at 508 applies a low-pass filter to the first reflected signal and the second reflected signal to produce a first filtered signal and a second filtered signal, respectively. The low-pass filter may remove electrical or thermal noise from the first and second reflected signals. The noise may be introduced in the first and second reflected signals by circuit components of the heart rate measurement device 100b. The low-pass filter may have a cutoff frequency that is higher than a typical heart rate. For example, the human heart rate is typically between 0.5 and 3 Hertz (Hz). If the heart rate measurement device 100b is used to measure the human heart rate, the cutoff frequency of the low-pass filter may be set to 4 Hz, thus capturing the 0.5 to 3 Hz band of human heart rate. Accordingly, heart rate information is not filtered out by the low-pass filtering.

The processor 110 then de-trends the first and second filtered signals to produce respective first and second de-trended signals at 510. De-trending the first and second filtered signals removes an identified trend in the signals and enables analysis of the signals to focus on fluctuations or variations in the signals as opposed to a trend in the signals. The first filtered signal may be de-trended by linearly fitting the first filtered signal and subtracting the linearly-fitted signal from the first filtered signal.

The processor 110, at 512, cross-correlates the first and second de-trended signals. Denoting the first de-trended signal as $D_1(n)$ and the second de-trended signal as $D_2(n)$, the cross-correlation function of the first de-trended signal and the second de-trended signal is:

$$XCorr(\tau) = \sum_{\tau=-\infty}^{\tau=+\infty} D_1(n)D_2(n-\tau). \quad \text{Equation (3)}$$

The processor 110 then identifies a maximum cross-correlation value and an index of the maximum cross-correlation value at 514. The maximum cross-correlation value may be the maximum value of the time-series correlation function (XCorr). The index may be the corresponding time index of the maximum cross-correlation value. The index may represent a time shift of the second de-trended signal that, when performed, results in a highest degree of similarity between the first de-trended signal and the second de-trended signal.

The processor 110 at 516 determines if the maximum cross-correlation value is greater than a threshold. The threshold may, for example, be a minimum correlation value such as 0.5. The threshold may be determined based on observed correlations in "no motion" conditions. Under these conditions, the first reflected signal has a strong signal component. The second reflected signal, on the other hand, has a poor signal component and has a heavy contribution of the noise component.

If the maximum cross-correlation value is below the threshold then the similarities between the first and second reflected signals may not be sufficient for performing motion compensation. Accordingly, if the maximum cross-correlation value is not greater than the threshold, the processor 110 at 518 determines the heart rate based on the first reflected signal as the heart rate signal.

If the maximum cross-correlation value is greater than the threshold, the processor 110 performs motion compensation as described herein. In motion compensation, the second de-trended signal is used to remove the additive noise affecting the first de-trended signal as a result of the motion.

At 520, the processor 110 shifts the second de-trended signal by the index of the maximum cross-correlation value. As a result, the first de-trended signal and the second de-trended signal become aligned to maximize their correlation.

The processor 110 obtains an adapting amplitude coefficient for the second de-trended signal at 522. The adapting amplitude coefficient minimizes the difference in energy between the first de-trended signal and the second de-trended signal. To obtain the adapting amplitude coefficient the following energy function is determined:

$$E(\alpha) = \int \left(D_1 - \frac{D_2}{\alpha}\right)^2. \quad \text{Equation (4)}$$

A minimum of the energy function is identified and the adapting amplitude coefficient is the input to the function (Coeff=α) corresponding to the minimum of the energy function. In the above equation, α minimizes the energy using the least squares technique. However, as may be recognized other frameworks for determining an energy minimizing coefficient may be used.

The processor 110 at 524 obtains a heart rate signal as the difference between the first de-trended signal and a quotient of the second de-trended signal and the adapting amplitude coefficient. The heart rate signal is accordingly determined as:

$$H = D_1 - \frac{D_2}{Coeff}. \quad \text{Equation (5)}$$

The processor 110 at 526 then determines the heart rate based on the heart rate signal (H) as described herein. Determining the heart rate may include counting a number of peaks and/or valleys of the heart rate signal in an interval (for example, a 15 second interval) and obtaining the heart rate based on that number.

The method described with reference to FIGS. 5A and 5B may be used when the heart measurement device 100b utilizes one first light source 106b for emitting light captured as the first reflected signal and one second light source 108b for emitting light captured as the second reflected signal. When the heart measurement device 100b operates two or more first light sources 106b and two or more second light sources 108b, the processor 110 receives from the photodetector 109b more than two reflected signals.

If two first light sources 106b and two second light sources 108b are used, the processor 110 receives two first reflected signals (denoted as $R_{11}$ and $R_{12}$) and two second reflected signals (denoted as $R_{21}$ and $R_{22}$).

Figure 6A:
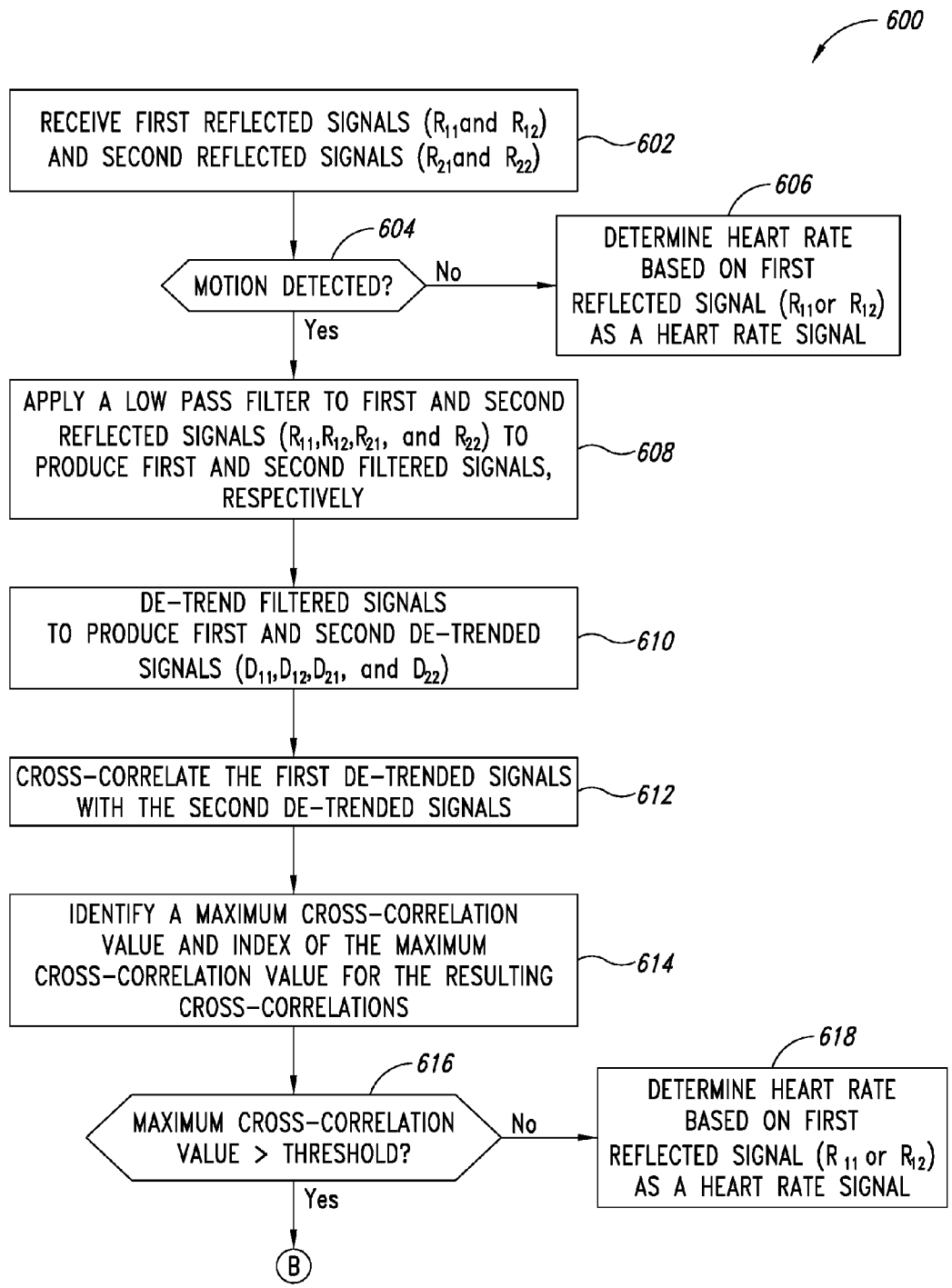
FIGS. 6A and 6B show a flow diagram of a method for compensating for motion in the heart rate measurement device.
Figure 6B:
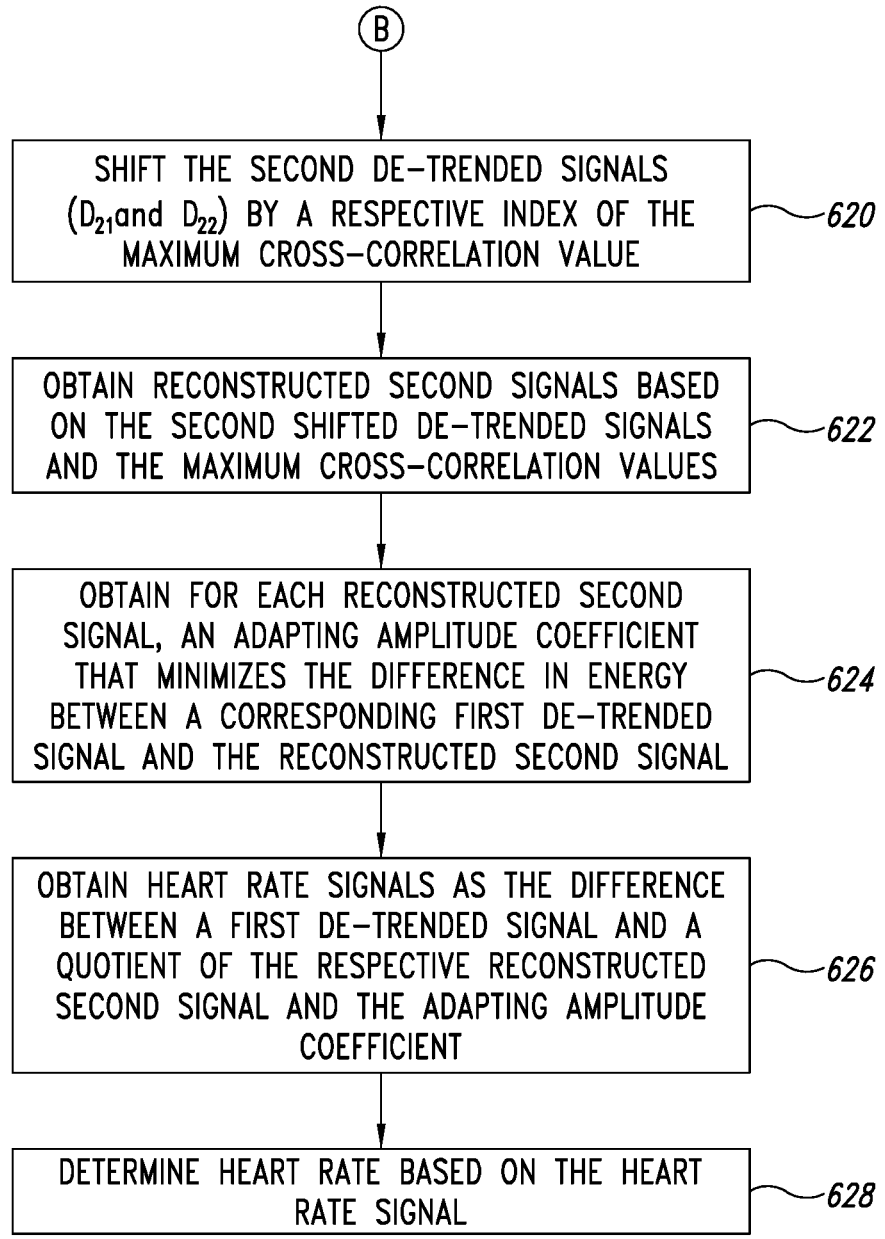

FIGS. 6A and 6B show a flow diagram of a method for compensating for motion in the heart rate measurement device 100b. At 602, the processor 110 receives the first reflected signals ($R_{11}$ and $R_{12}$) and the second reflected signals ($R_{21}$ and $R_{22}$). The processor 110 then determines if motion is detected at 604. If a negative determination is made, at 606, the processor 110 determines the heart rate based on a first reflected signal ($R_{11}$ or $R_{12}$) as a heart rate signal.

If a positive determination is made, at 608 the processor 110 applies a low pass filter to the first and second reflected signals ($R_{11}$, $R_{12}$, $R_{21}$ and $R_{22}$) to produce filtered signals. At 610, the processor de-trends the filtered signals to produce first de-trended signals ($D_{11}$ and $D_{12}$) and second de-trended signals ($D_{21}$ and $D_{22}$). Each signal is individually filtered and de-trended.

At 612, the processor 110 cross-correlates the first de-trended signals with the second de-trended signals. The cross-correlation will produce four cross-correlation functions that are as follows: $XCorr_1=XCorr(D_{11}, D_{21})$, $XCorr_2=XCorr(D_{11}, D_{22})$, $XCorr_3=XCorr(D_{12}, D_{21})$ and $XCorr_4=XCorr(D_{12}, D_{22})$.

For each resulting cross-correlation, the processor 110 at 614 identifies a maximum cross-correlation value and index of the maximum cross-correlation value. The indices of the maximum cross-correlation values and the maximum cross-correlation values are obtained as $[Ind_1, Val_1]=\max(XCorr_1)$, $[Ind_2, Val_2]=\max(XCorr_2)$, $[Ind_3, Val_3]=\max(XCorr_3)$ and $[Ind_4, Val_4]=\max(XCorr_4)$.

The processor 110 at 616 determines whether a maximum cross-correlation value of the identified maximum cross-correlation values exceeds a threshold. If a negative determination is made, the processor 110 at 618 determines the heart rate based on a first reflected signal. That is, the heart rate may be determined using $R_{11}$ or $R_{12}$.

If a positive determination is made, the processor 110 performs motion compensation. The processor 110 shifts the second de-trended signals by a respective index of the maximum cross-correlation value at 620. $D_{21}$ may be shifted by $Ind_1$ or $Ind_3$. Further, $D_{22}$ may be shifted by $Ind_2$ or $Ind_4$.

At 622, the processor 110 obtains reconstructed second signals ($C_1$ and $C_2$) based on the second shifted de-trended signals and the maximum cross-correlation values. The reconstructed second signals are obtained as:

$$C_1 = \frac{R_{11} \cdot Val_1 + R_{12} \cdot Val_2}{Val_1 + Val_2} \qquad \text{Equation (6)}$$

$$C_2 = \frac{R_{11} \cdot Val_3 + R_{12} \cdot Val_4}{Val_3 + Val_4}.$$

At 624, for each reconstructed second signal, the processor 110 obtains an adapting amplitude coefficient that minimize the difference in energy between a corresponding first de-trended signal and the reconstructed second signal. The difference in energy between a first de-trended signal and a corresponding reconstructed second signal for each pair of the first de-trended signal and the corresponding reconstructed second signal as described herein. The energy is determined as:

$$E_1(\alpha) = \int \left(D_{11} - \frac{C_1}{\alpha}\right)^2 \qquad \text{Equation (7)}$$

$$E_2(\alpha) = \int \left(D_{12} - \frac{C_2}{\alpha}\right)^2$$

A first adapting amplitude coefficient ($Coeff_1=a_1$) that minimizes $E_1(\alpha)$ is obtained as $[a_1, E_{1min}]=\min(E_1(\alpha))$ and a second adapting amplitude coefficient ($Coeff_2=\alpha_2$) that minimizes $E_2(\alpha)$ is obtained as $[\alpha_2, E_{2min}]=\min(E_2(\alpha))$.

At 626, the processor 110 obtains heart rate signals. Each heart rate signal is a difference between a first de-trended signal and a quotient of the respective reconstructed second signal and the adapting amplitude coefficient. A first heart rate signal is obtained as $$H_1 = D_{11} - \frac{C_1}{Coeff_1}$$

and a second heart rate signal is obtained as $$H_2 = D_{12} - \frac{C_2}{Coeff_2}.$$

The processor 110 at 628 determines the heart rate based on a heart rate signal.

Figure 7:
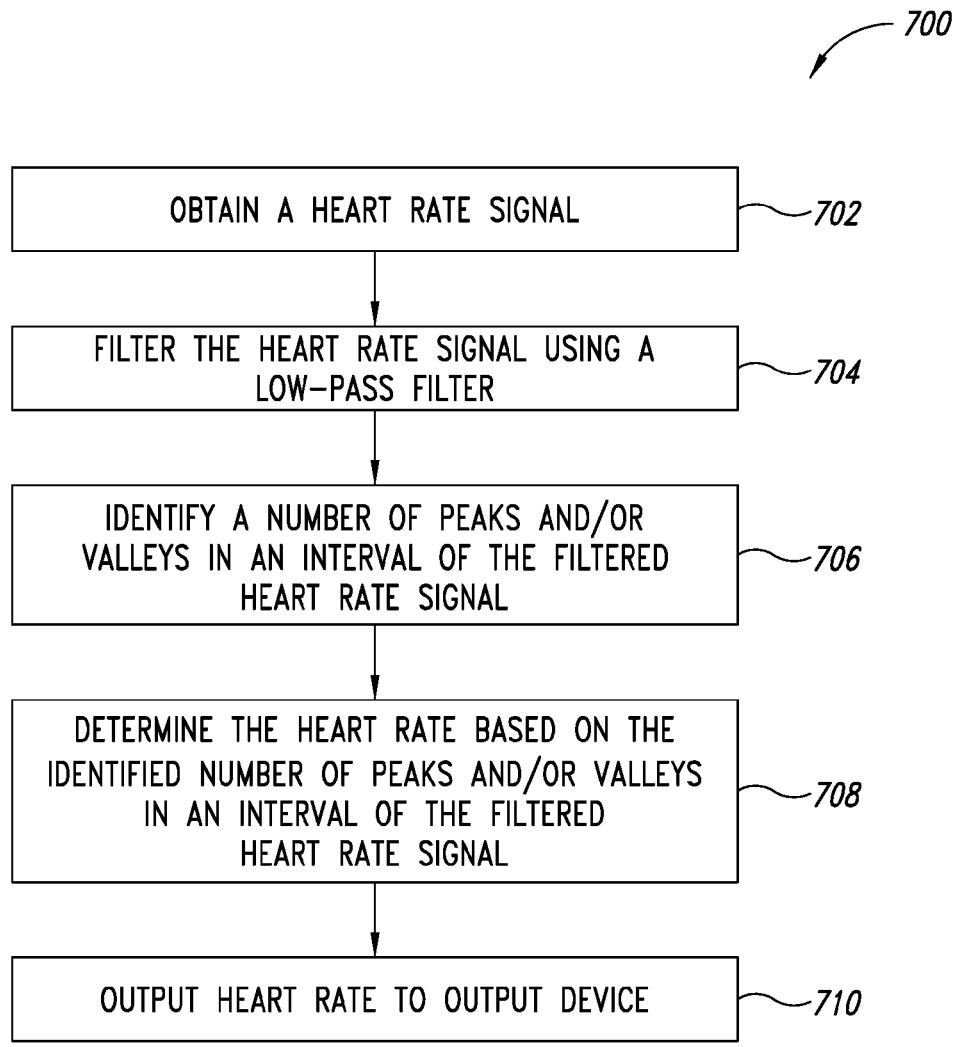
FIG. 7 shows a flow diagram of a method for determining the heart rate based on a heart rate signal.

FIG. 7 shows a flow diagram of a method for determining the heart rate based on a heart rate signal. In the method 700, the processor 110 obtains a heart rate signal as described herein at 702. The processor 110 filters the heart rate signal using a low-pass filter at 704. The cutoff frequency of the low-pass filter may be higher than a typical range of the heart rate. The processor 110 at 706 identifies a number of peaks and/or valleys in an interval of the filtered heart rate signal. At 708, the processor 110 determines the heart rate based on the identified a number of peaks and/or valleys in an interval of the filtered heart rate signal. After determining the heart rate, the processor 110 at 710 outputs the heart rate to an output device, such as the output device 114 described with reference to FIG. 3 herein. The displayed heart rate may be used by health personnel for evaluating the health of the biological body, such as a human being or an animal.

The intensity of the emitted light having the first wavelength and the emitted light having the second wavelength may be regulated such that the two lights, when reflected, arrive at a photodetector having comparable DC values. The DC values may be higher than a spectral sensitivity of the photodetector. To ensure that the detected DC values are comparable, the emitted intensity of the light having the first wavelength may be set to be greater than the emitted light having the second wavelength.

The various embodiments described above can be combined to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device comprising:
a first light source configured to emit light having a first wavelength at a biological body, the first wavelength being associated with a first absorption coefficient for blood components;
a second light source configured to emit light having a second wavelength at the biological body, the second wavelength being associated with a second absorption coefficient for the blood components that is less than the first absorption coefficient;
a photodetector configured to capture a first reflected signal as a result of the light having the first wavelength being reflected from the biological body and capture a second reflected signal as a result of the light having the second wavelength being reflected from the biological body; and
a processor coupled to the photodetector and configured to receive the first reflected signal and the second reflected signal from the photodetector, obtain an amplitude adapting coefficient for the second reflected signal, obtain a heart rate signal as a difference between the first reflected signal, and a quotient of the second reflected signal and the amplitude adapting coefficient, and determine a heart rate of the biological body based on the heart rate signal.

2. The device of claim 1, wherein the amplitude adapting coefficient is a divisor of the second reflected signal that minimizes a difference in energy between the first reflected signal and the quotient of the second reflected signal and the amplitude adapting coefficient.

3. The device of claim 1, wherein the processor is further configured to:
cross-correlate the first reflected signal and the second reflected signal to produce a cross-correlation function between the first reflected signal and the second reflected signal;
identify a maximum of the cross-correlation function;
identify a time index corresponding to the maximum of the cross-correlation function; and
shift the second reflected signal by the time index prior to obtaining the heart rate signal using the second reflected signal shifted by the time index.

4. The device of claim 1, wherein the processor is further configured to:
low-pass filter the first reflected signal and the second reflected signal; and
de-trend the first reflected signal and the second reflected signal.

5. The device of claim 4, wherein a cutoff frequency of the low pass filter is 4 Hertz or lower.

6. The device of claim 1, further comprising a motion detector coupled to the processor and configured to output a signal to the processor indicating whether the device was displaced, wherein:
the processor is further configured to determine the heart rate based on the heart rate signal if the signal to the processor indicates that the device was displaced.

7. The device of claim 1, further comprising an output device coupled to the processor and configured to receive the heart rate from the processor and display the heart rate, wherein the processor is further configured to:
identify a number of peaks and/or valleys in an interval of the heart rate signal; and
determine the heart rate based on the number of peaks and/or valleys in the interval.

8. A method, comprising:
emitting light having a first wavelength at a biological body, the first wavelength being associated with a first absorption coefficient for blood components;
capturing a first reflected signal as a result of the light having the first wavelength being reflected from the biological body;
emitting light having a second wavelength at the biological body, the second wavelength being associated with a second absorption coefficient for the blood components that is less than the first absorption coefficient;
capturing a second reflected signal as a result of the light having the second wavelength being reflected from the biological body;
before obtaining a heart rate signal, scaling the second reflected signal by a reciprocal of an amplitude adapting coefficient;
obtaining the heart rate signal as a difference between the first reflected signal and the second reflected signal that is scaled by the reciprocal of the amplitude adapting coefficient; and
determining a heart rate of the biological body based on the heart rate signal.

9. The method of claim 8, wherein the amplitude adapting coefficient is a divisor of the second reflected signal that minimizes a difference in energy between the first reflected signal and the quotient of the second reflected signal and the amplitude adapting coefficient.

10. The method of claim 8, further comprising:
time shifting the second reflected signal prior to obtaining the heart rate signal using the time shifted second reflected signal.

11. The method of claim 10, wherein the second reflected signal is shifted by a time index corresponding to a maximum cross-correlation value between the first reflected signal and the second reflected signal.

12. The method of claim 8, further comprising:
filtering the first and second reflected signals; and
de-trending the first and second reflected signals.

13. A system comprising:
a first light source;
a second light source;
a photodetector;
a processor; and
a computer-readable storage medium having stored thereon instructions that, when executed by the processor, cause the processor to:
instruct the first light source to emit light having a first wavelength at a biological body, the first wavelength being associated with a first absorption coefficient for blood components;
instruct the second light source to emit light having a second wavelength at the biological body, the second wavelength being associated with a second absorption coefficient for the blood components that is less than the first absorption coefficient;
receive a first reflected signal captured by the photodetector as a result of the light having the first wavelength being reflected from the biological body and a second reflected signal captured by the photodetector as a result of the light having the second wavelength being reflected from the biological body;

obtain an amplitude adapting coefficient for the second reflected signal;

adjust an amplitude of the second reflected signal by the amplitude adapting coefficient to obtain an amplitude-adjusted second reflected signal;

obtain a heart rate signal based on the first reflected signal and the amplitude-adjusted second reflected signal; and determine a heart rate of the biological body based on the heart rate signal.

14. The system of claim 13, wherein the instructions further cause the processor to obtain the heart rate signal as a difference between the first reflected signal and the amplitude-adjusted second reflected signal.

15. The system of claim 13, wherein the instructions further cause the processor to:

low-pass filter the first and second reflected signals to respectively produce first and second filtered signals; and de-trend the first and second filtered signals ahead of obtaining the heart rate signal.

16. The system of claim 13, wherein the first wavelength is between 500 and 580 nanometers (nm) and the second wavelength is between 680 and 700 nm.

17. The system of claim 13, wherein:

the system further comprises:

a third light source;

a fourth light source;

the instructions further cause the processor to:

instruct the third light source to emit light having the first wavelength;

instruct the fourth light source to emit light having the second wavelength; and receive a third reflected signal captured by the photodetector as a result of the light emitted by the third source being reflected from the biological body and a fourth reflected signal captured by the photodetector as a result of the light emitted by the fourth source being reflected from the biological body.

18. The system of claim 17, wherein the instructions further cause the processor to:

cross-correlate the first and third reflected signals with the second and fourth reflected signals to obtain a plurality of cross-correlation functions;

identify a plurality of maximum cross-correlation values of the respective plurality cross-correlation functions, the plurality of maximum cross-correlation values including at least a first, second, third and fourth maximum cross-correlation value, the first, second, third and fourth maximum cross-correlation values having associated first, second, third and fourth indices, respectively;

determine that a maximum cross-correlation value of the plurality of maximum cross-correlation values exceeds a threshold; and shift the second reflected signal by the second index and shift the fourth reflected signal by the fourth index to produce a second shifted signal and a fourth shifted signal.

19. The system of claim 18, wherein the instructions further cause the processor to:

obtain a first reconstructed signal based on the first and third reflected signals and the first and third maximum cross-correlation values and a second reconstructed signal based on the first and third reflected signals and the second and fourth maximum cross-correlation values;

identify a first amplitude adapting coefficient of the first reconstructed signal and a second amplitude adapting coefficient of the second reconstructed signal; and scale the first reconstructed signal by the first amplitude adapting coefficient and the second reconstructed signal by the second amplitude adapting coefficient to respectively produce first and second scaled signals.

20. The system of claim 19, wherein obtaining the heart rate signal includes obtaining a first heart rate signal as a difference between the first reflected signal and the first reconstructed signal and a second heart rate signal as a difference between the second reflected signal and the second reconstructed signal.

21. The system of claim 20, wherein determining the heart rate of the biological body further includes determining the heart rate of the biological body based at least in part on the first heart rate signal or the second heart rate signal.

22. A device comprising:

a first light source configured to emit light having a first wavelength at a biological body, the first wavelength being associated with a first absorption coefficient for blood components;

a second light source configured to emit light having a second wavelength at the biological body, the second wavelength being associated with a second absorption coefficient for the blood components that is less than the first absorption coefficient;

a photodetector configured to capture a first reflected signal as a result of the light having the first wavelength being reflected from the biological body and capture a second reflected signal as a result of the light having the second wavelength being reflected from the biological body; and a processor coupled to the photodetector and configured to:

receive the first reflected signal and the second reflected signal from the photodetector, cross-correlate the first reflected signal and the second reflected signal to produce a cross-correlation function between the first reflected signal and the second reflected signal, identify a maximum of the cross-correlation function, identify a time index corresponding to the maximum of the cross-correlation function, shift the second reflected signal by the time index, obtain a heart rate signal as a difference between the first reflected signal and the second reflected signal shifted by the time index, and determine a heart rate of the biological body based on the heart rate signal.

23. The device of claim 22, further comprising a motion detector coupled to the processor and configured to output a signal to the processor indicating whether the device was displaced, wherein:

the processor is further configured to determine the heart rate based on the heart rate signal if the signal to the processor indicates that the device was displaced.

24. The device of claim 22, further comprising an output device coupled to the processor and configured to receive the heart rate from the processor and display the heart rate, wherein the processor is further configured to:

identify a number of peaks and/or valleys in an interval of the heart rate signal; and determine the heart rate based on the number of peaks and/or valleys in the interval.

25. A method, comprising:
emitting light having a first wavelength at a biological body, the first wavelength being associated with a first absorption coefficient for blood components;
capturing a first reflected signal as a result of the light having the first wavelength being reflected from the biological body;
emitting light having a second wavelength at the biological body, the second wavelength being associated with a second absorption coefficient for the blood components that is less than the first absorption coefficient;
capturing a second reflected signal as a result of the light having the second wavelength being reflected from the biological body;
time shifting the second reflected signal by a time index corresponding to a maximum cross-correlation value between the first reflected signal and the second reflected signal;
obtaining a heart rate signal as a difference between the first reflected signal and the time-shifted second reflected signal; and
determining a heart rate of the biological body based on the heart rate signal.

26. The method of claim 25, further comprising:
filtering the first and second reflected signals; and
de-trending the first and second reflected signals.

27. A system comprising:
a first light source;
a second light source;
a photodetector;
a processor; and
a computer-readable storage medium having stored thereon instructions that, when executed by the processor, cause the processor to:
instruct the first light source to emit light having a first wavelength at a biological body, the first wavelength being associated with a first absorption coefficient for blood components;
instruct the second light source to emit light having a second wavelength at the biological body, the second wavelength being associated with a second absorption coefficient for the blood components that is less than the first absorption coefficient;
receive a first reflected signal captured by the photodetector as a result of the light having the first wavelength being reflected from the biological body and a second reflected signal captured by the photodetector as a result of the light having the second wavelength being reflected from the biological body;
shift the second reflected signal by a time index corresponding to a maximum cross-correlation value between the first reflected signal and the second reflected signal to obtain a second shifted signal;
obtain a heart rate signal based on the first reflected signal and the second shifted signal; and
determine a heart rate of the biological body based on the heart rate signal.

28. The system of claim 27, wherein:
the system further comprises:
a third light source;
a fourth light source;
the instructions further cause the processor to:
instruct the third light source to emit light having the first wavelength;
instruct the fourth light source to emit light having the second wavelength; and
receive a third reflected signal captured by the photodetector as a result of the light emitted by the third source being reflected from the biological body and a fourth reflected signal captured by the photodetector as a result of the light emitted by the fourth source being reflected from the biological body.

29. The system of claim 28, wherein the instructions further cause the processor to:
cross-correlate the first and third reflected signals with the second and fourth reflected signals to obtain a plurality of cross-correlation functions;
identify a plurality of maximum cross-correlation values of the respective plurality cross-correlation functions, the plurality of maximum cross-correlation values including at least a first, second, third and fourth maximum cross-correlation value, the first, second, third and fourth maximum cross-correlation values having associated first, second, third and fourth indices, respectively;
determine that a maximum cross-correlation value of the plurality of maximum cross-correlation values exceeds a threshold; and
shift the fourth reflected signal by the fourth index to produce a fourth shifted signal, wherein the time index corresponding to the maximum cross-correlation value between the first reflected signal and the second reflected signal is the second index.

30. The system of claim 29, wherein the instructions further cause the processor to:
obtain a first reconstructed signal based on the first and third reflected signals and the first and third maximum cross-correlation values and a second reconstructed signal based on the first and third reflected signals and the second and fourth maximum cross-correlation values;
identify a first amplitude adapting coefficient of the first reconstructed signal and a second amplitude adapting coefficient of the second reconstructed signal; and
scale the first reconstructed signal by the first amplitude adapting coefficient and the second reconstructed signal by the second amplitude adapting coefficient to respectively produce first and second scaled signals.

* * * * *